US00PP22730P3

(12) United States Plant Patent

Zaiger et al.

(10) Patent No.: US PP22,730 P3

(45) Date of Patent: May 15, 2012

(54) INTERSPECIFIC TREE NAMED 'MACY-COT'

(50) Latin Name: **Interspecific *Prunus* species**
Varietal Denomination: Macy-Cot

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 131 days.

(21) Appl. No.: 12/807,007

(22) Filed: Aug. 26, 2010

(65) Prior Publication Data

US 2012/0054926 P1 Mar. 1, 2012

(51) Int. Cl.
*A01H 5/00* (2006.01)

(52) U.S. Cl. ..... Plt./180

(58) Field of Classification Search ..... Plt./180
See application file for complete search history.

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Regular production of large size fruit.
3. Fruit with good flavor and eating quality.
4. Fruit with good handling and storage ability.
5. The interspecific tree being self-fruitful, producing fruit with its own pollen.

1 Drawing Sheet

Botanical description: Interspecific *Prunus* species.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of plum and apricots, which are known to us, and mentioned herein, 'Flaming Gold' Apricot (U.S. Plant Pat. No. 2,822), 'King Cot' Apricot (non-patented), 'Red Beaut' Plum (U.S. Plant Pat. No. 2,539) and the proprietary selected seedlings '25ED21' and '32GH296'.

STATEMENT REGARDING FEDERALLY SPONSORED RESEARCH AND DEVELOPMENT

Not applicable.

ORIGIN OF THE VARIETY

The new and distinct variety of interspecific tree, [*Prunus armeniaca*×(*Prunus salicina*×*Prunus armeniaca*)] was originated from a first generation cross between the proprietary seedling selections with the field identification numbers '25ED21' and '36GH296'. The seed parent (25ED21) originated from crosses between 'King Cot' Apricot (non-patented) and 'Flaming Gold' Apricot (U.S. Plant Pat. No. 2,822). The pollen parent (36GH296) originated as an open pollinated seedling from a proprietary seedling selection from the cross of 'Red Beaut' Plum (U.S. Plant Pat. No. 2,539) with an apricot of unknown parentage. We planted and maintained a large group of these first generation seedlings on their own root system and under close and careful observation one such seedling, which is the present variety, exhibited desirable tree and fruit characteristics and was selected in 2003 for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree (Apricot× Plumcot) is of large size, vigorous upright growth and a productive and regular bearer of large size fruit with good flavor and eating quality. The fruit is further characterized by its firm flesh, good handling and shipping quality and being relatively uniform in size throughout the tree. In comparison to its seed parent (25ED21) the new variety has a more consistent fruit crop and the fruit matures approximately 3 days earlier. In comparison to its pollen parent '36GH296' the variety has firmer and larger size fruit.

PHOTOGRAPH OF THE VARIETY

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color.

Tree:

*Size.*—Large, usually pruned to 3 to 3.5 meters in height and width for economical harvesting of fruit.

*Vigor.*—Vigorous, growth of 1.5 to 2 meters in height the first growing season. Varies with fertility and type of soil, climatic conditions and cultural practices.

*Form.*—Upright, usually pruned to vase shape.

*Branching habit.*—Upright, crotch angle approximately 30°, increases with heavy crop load.

*Productivity.*—Productive, thinning and spacing of fruit desirable. Fruit set varies with climatic conditions during blooming period.

*Bearer.*—Regular, has had an adequate crop 5 consecutive years. No alternate bearing observed.

*Fertility.*—Self fertile.

*Density.*—Medium dense, usually pruned to vase shape to allow more sunlight to center of tree to enhance fruit color and health of fruit spurs.

*Hardiness.*—Tree grown in USDA Hardiness Zone 9. Hardy in all stone fruit growing areas of California. Winter chilling requirement approximately 700 hours at or below 45° F.

Trunk:

*Size.*—Medium to large. Average circumference 50.8 cm at 25.8 cm above ground level on a 7 year old tree.

*Stocky.*—Medium stocky.

*Texture.*—Medium shaggy, increases with age of growth.

*Color.*—Varies from 10YR 2/2 to 2.5Y 5/2.

Branches:

*Size.*—Medium. Average circumference 20.3 cm at 1.2 meters above ground. Crotch angle approximately 30°, increases with heavy crop load.

*Surface texture.*—New growth relatively smooth. Mature growth medium rough, roughness increases with age.

*Lenticels.*—Average number 42 in a 25.8 sq cm surface area of branch. Average length 4.1 mm. Average width 1.6 mm. Color varies from 10YR 5/6 to 2.5Y 6/6.

*Color.*—New growth varies from 7.5R 2/8 to 5GY 5/8, depending on degree of exposure to sunlight. Old growth varies from 7.5YR 2/4 to 10YR 4/2, varies with age of growth.

Leaves:

*Size.*—Medium to large. Average length 67.2 mm. Average width 57.4 mm.

*Form.*—Ovate.

*Apex.*—Acuminate.

*Base.*—Cuneate.

*Margin.*—Serrate.

*Thickness.*—Medium.

*Surface texture.*—Upper surface relatively smooth, very slightly indented over midrib and leaf veins, glabrous. Lower surface relatively smooth, except for small ridges caused by midrib and pinnate venation, glabrous.

*Petiole.*—Average length 25.7 mm. Average width 1.4 mm. Longitudinally grooved. Surface — glabrous. Color varies from 5R 3/2 to 5R 2/4.

*Glands.*—Type — reniform. Size — small. Average length 0.4 mm. Average diameter 0.2 mm. Number — average 2, varies from 1 to 3. Located primarily on upper portion of petiole, base of leaf blade. Color varies from 2.5GY 5/6 to 7.5R 3/4.

*Stipules.*—Number — average 2 per leaf axial. Average length 7.0 mm. Margin — serrate. Color varies from 10Y 7/6 to 7.5R 4/6.

*Color.*—Upper surface varies from 10GY 3/4 to 7.5GY 3/6. Lower surface varies from 2.5G 3/4 to 10GY 3/4. Midvein color varies from 2.5GY 7/4 to 5GY 7/4.

Flower buds:

*Size.*—Medium to large. Average length 14.5 mm. Average diameter 10.4 mm.

*Hardiness.*—Hardy with respect to California winters.

*Form.*—Conical, becoming elongated just before opening.

*Pedicel.*—Short. Average length 1.7 mm. Average width 2.0 mm. Color varies from 2.5GY 8/6 to 2.5GY 7/6.

*Color.*—Varies from 5RP 6/12 to 7.5RP 8/4, color fades with age.

*Number of buds per spur.*—Varies from 5 to 13, varies with age of spur.

Flowers:

*Blooming period.*—Date of First Bloom Feb. 16, 2010. Date of Petal Fall Feb. 24, 2010, varies slightly with climatic conditions.

*Size.*—Medium to large. Average height 18.8 mm. Average diameter 26.9 mm.

*Petals.*—Number — 5, alternately arranged to sepals. Size — medium to large. Average length 14.1 mm. Average width 17.2 mm. Form — orbicular. Margin — sinuate. Color varies from 10RP 9/2 to 10RP 8/4, fades with age of flower.

*Sepals.*—Number — 5, alternately arranged to petals. Size — medium. Average length 6.0 mm. Average width 6.7 mm. Shape — ovate, apex rounded. Margin — entire. Both upper and lower surfaces glabrous. Color — upper surface varies from 10RP 3/6 to 5R 2/8. Lower surface varies from 5R 2/8 to 7.5R 2/8.

*Stamens.*—Average number per flower 29. Average filament length 12.6 mm. Filament color N 9.5/ (white). Anther color varies from 5Y 8/10 to 5Y 7/12.

*Pollen.*—Self fertile, fruit set while under a bag. Color varies from 2.5Y 7/10 to 5Y 7/10.

*Pistil.*—Normally one. Surface pubescent. Average length 15.0 mm. Position of stigma average of 1.4 mm below anthers. Color varies from 7.5Y 8.5/4 to 10Y 8.5/4.

*Fragrance.*—Moderate.

*Color.*—Varies from 10RP 9/2 to N 9.5/(white), fades with age of flower.

*Number flowers per flower bud.*—Average 2, varies from 1 to 3.

*Pedicel.*—Average length 1.9 mm. Average width 2.2 mm. Color varies from 10Y 7/6 to 2.5GY 7/6.

Fruit:

*Maturity when described.*—Firm ripe.

*Date of first picking.*—Jun. 1, 2010.

*Date of last picking.*—Jun. 6, 2010, varies slightly with climatic conditions.

*Size.*—Large. Average diameter axially 64.7 mm. Average transversely in suture plane 66.7 mm. Average across suture plane 62.9 mm. Average weight 159.0 grams, average weight varies with fertility of the soil, amount of thinning and climatic conditions.

*Form.*—Nearly globose, slightly elongated and compressed in suture plane.

*Suture.*—Lipped, extends from base to apex.

*Ventral surface.*—Lipped, well sealed.

*Apex.*—Slightly retuse.

*Base.*—Retuse.

*Stem cavity.*—Rounded. Average depth 4.4 mm. Average diameter 6.2 mm.

Stem:

*Size.*—Small to medium. Average length 8.7 mm. Average diameter 4.7 mm.

*Color.*—Varies from 10Y 6/8 to 2.5GY 6/8.

Flesh:

*Ripens.*—Evenly.

*Texture.*—Firm, meaty.

*Fibers.*—Few, small, tender.

*Firmness.*—Firm, firmer than most commercial apricots.

*Aroma.*—Moderate.

*Amydgalin.*—Undetected.

*Eating quality.*—Good.

*Flavor.*—Good, with a good balance between acid and sugar.

*Juice.*—Moderate amount, enhances flavor.

*Brix.*—Average Brix 13.0°, varies slightly with amount of fruit per tree and climatic conditions.

*Color.*—Varies from 7.5YR 7/6 to 10YR 9/2. Pit cavity varies from 7.5YR 6/4 to 7.5YR 7/12.

Skin:

*Thickness.*—Medium.

*Surface.*—Smooth.

*Pubescence.*—Light amount, very short in length.

*Tendency to crack.*—None.

*Color.*—Ground color varies from 7.5YR 7/8 to 7.5YR 6/8. Overspread with 7.5R 5/8.

*Tenacity.*—Tenacious to flesh.

*Astringency.*—Undetected.

Stone:

*Type.*—Freestone.

*Size.*—Large. Average length 32.7 mm. Average width 25.2 mm. Average thickness 18.7 mm.

*Form.*—Ovoid.

*Base.*—Flat.

*Apex.*—Rounded.

*Surface.*—Slightly pitted throughout. Pits vary from round to elongated.

*Sides.*—Unequal, one side extending further from suture plane.

*Ridges.*—Small, narrow ridge next to groove on each side of suture, extends from base to apex.

*Tendency to split.*—None.

*Color.*—7.5YR 3/2, when dry.

*Pit cavity.*—Average length 35.2 mm. Average depth 11.4 mm.

Kernel:

*Size.*—Large. Average length 22.5 mm. Average width 14.9 mm. Average depth 12.6 mm.

*Shape.*—Ovate.

*Viability.*—Viable, complete embryo development.

*Skin.*—Color varies from 5Y 9/2 to 5Y 8/4.

Use:

*Dessert.*—Market — local and long distance.

Keeping quality: Good, held firm in cold storage 3 weeks at 38° to 42° F. without shriveling, internal breakdown of flesh or appreciable loss of eating quality.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct interspecific tree, substantially as illustrated and described.

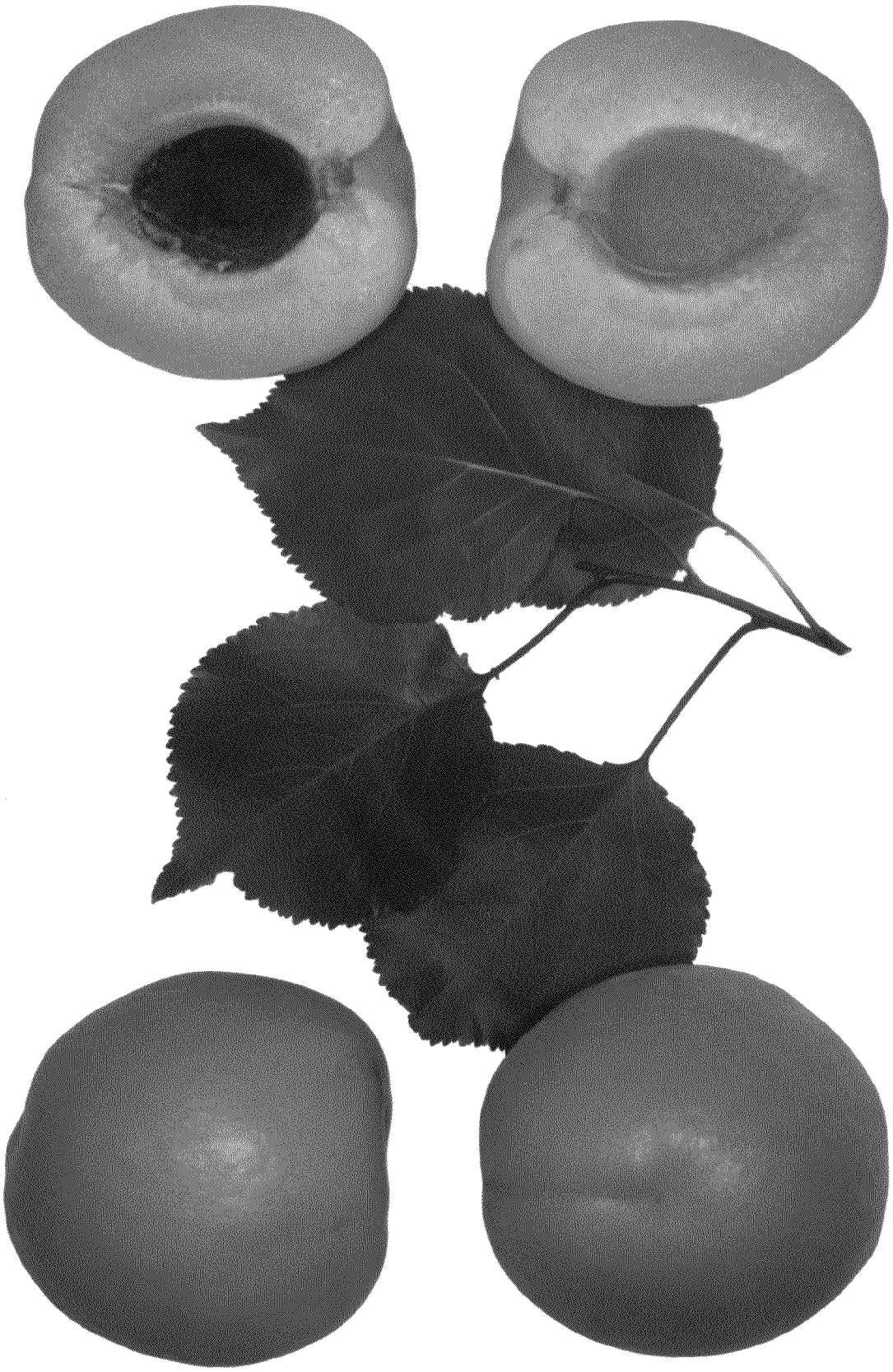

* * * * *